United States Patent
Pang et al.

(10) Patent No.: US 11,585,812 B2
(45) Date of Patent: Feb. 21, 2023

(54) INFLUENZA VIRUS DETECTION CHIP AND METHOD FOR DETECTING INFLUENZA VIRUS THEREWITH

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Fengchun Pang, Beijing (CN); Chuncheng Che, Beijing (CN); Hailin Xue, Beijing (CN); Xibin Shao, Beijing (CN); Peizhi Cai, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 1191 days.

(21) Appl. No.: 16/086,322

(22) PCT Filed: Feb. 7, 2018

(86) PCT No.: PCT/CN2018/075642
§ 371 (c)(1),
(2) Date: Sep. 19, 2018

(87) PCT Pub. No.: WO2019/007062
PCT Pub. Date: Jan. 10, 2019

(65) Prior Publication Data
US 2021/0181198 A1 Jun. 17, 2021

(30) Foreign Application Priority Data
Jul. 5, 2017 (CN) .......................... 201710541533.4

(51) Int. Cl.
*G01N 33/569* (2006.01)
*G01N 21/64* (2006.01)

(52) U.S. Cl.
CPC ... *G01N 33/56983* (2013.01); *G01N 21/6428* (2013.01); *G01N 2021/6439* (2013.01); *G01N 2800/26* (2013.01)

(58) Field of Classification Search
None
See application file for complete search history.

(56) References Cited

U.S. PATENT DOCUMENTS

| | | |
|---|---|---|
| 9,029,168 B2 | 5/2015 | McAlpine et al. |
| 2012/0156688 A1 | 6/2012 | McAlpine et al. |
| 2016/0223538 A1 | 8/2016 | McAlpine et al. |
| 2016/0289304 A1 | 10/2016 | Bucher et al. |

FOREIGN PATENT DOCUMENTS

| | | |
|---|---|---|
| CN | 101701957 A | 5/2010 |
| CN | 104649253 A | 5/2015 |
| CN | 105044072 A | 11/2015 |
| CN | 105242047 A | 1/2016 |
| CN | 105286803 A | 2/2016 |
| CN | 106226272 A | 12/2016 |
| CN | 105242047 B | 5/2017 |
| CN | 105044072 B | 8/2017 |
| CN | 207215705 U | 4/2018 |
| WO | 2017112941 A1 | 6/2017 |

OTHER PUBLICATIONS

Search Report and Written Opinion for International Application No. PCT/CN2018/075642 dated Apr. 12, 2018.
Eden Morales-Narvaez, et al., "Photoluminescent Lateral-Flow Immunoassay Revealed by Graphene Oxide: Highly Sensitive Paper-Based Pathogen Detection", Anal. Chem., 2015 87 (16), pp. 8573-0477 (abstract only).
First Office Action for Chinese Patent Application No. 201710541533.4 dated May 5, 2019.
Wang, Shu-Xian et al., "Research of Immunobiosensor for Vibrio Parahaemolyticus and Edwardsiella Tarda Simultaneous Detection Basing on Graphene Oxide", Journal of Agricultural Catastrophology, 2017, vol. 7, No. 2, 18-21,24.
Zhuan Zhuan Shi et al., "A one-piece lateral flow impedimetric test strip for label-free clenbuterol detection", Analytical Methods, 2015, 7, pp. 4957-4964, A Royal Society of Chemistry.

*Primary Examiner* — Nicole Kinsey White
(74) *Attorney, Agent, or Firm* — Calfee, Halter & Griswold LLP

(57) ABSTRACT

There is provided an influenza virus detection chip and a method for detecting influenza virus therewith. An influenza virus detection chip including: a graphene oxide film; a first pad disposed on one side of the graphene oxide film in a first direction; and a first electrode and a second electrode, connected to both ends of the graphene oxide film in a second direction perpendicular to the first direction, wherein a first monoclonal antibody with a fluorescent label is included in the first pad, and a second monoclonal antibody is included in the graphene oxide film, and wherein the fluorescent label includes a C=C—C=C conjugated double bond.

20 Claims, 2 Drawing Sheets

INFLUENZA VIRUS DETECTION CHIP AND METHOD FOR DETECTING INFLUENZA VIRUS THEREWITH

CROSS REFERENCE

The present application is based upon International Application No. PCT/CN2018/075642, filed on Feb. 7, 2018, which is based upon and claims priority to Chinese Patent Application No. 201710541533.4, filed on Jul. 5, 2017, and the entire contents thereof are incorporated herein by reference.

TECHNICAL FIELD

The present disclosure relates to the field of influenza virus detection, in particular, to an influenza virus detection chip and a method for detecting influenza virus therewith.

BACKGROUND

Influenza is an acute respiratory infection caused by influenza virus, and it is also a disease that is highly contagious and spreads rapidly. The influenza is more popular generally in autumn and winter seasons, and the complications and deaths caused thereby are very serious. The disease is caused by influenza virus and can be divided into three types: A, B, and C. The type A virus often undergoes antigenic variation, is highly contagious, spreads rapidly, and is prone to widespread epidemics. The infants, the elderlies, and patients with cardiopulmonary diseases having influenza are prone to serious complications such as pneumonia and cause death.

At present, the detection of influenza virus is mainly carried out by colloidal gold immunochromatography, ELISA, PCR and the like. Colloidal gold immunochromatography requires a large amount of influenza virus to accumulate at the detection line until color development.

It should be noted that, information disclosed in the above background portion is provided only for better understanding of the background of the present disclosure, and thus it may contain information that does not form the prior art known by those ordinary skilled in the art.

SUMMARY

The present disclosure provides an influenza virus detection chip and a method for detecting influenza virus using the influenza virus detection chip.

According to one aspect, the present disclosure provides an influenza virus detection chip including:

a graphene oxide film;

a first pad disposed on one side of the graphene oxide film in a first direction; and a first electrode and a second electrode, connected to both ends of the graphene oxide film in a second direction perpendicular to the first direction, wherein a first monoclonal antibody with a fluorescent label is included in the first pad, and a second monoclonal antibody is included in the graphene oxide film, and wherein the fluorescent label includes a C=C—C=C conjugated double bond.

In one embodiment, the influenza virus detection chip further includes a first substrate, the graphene oxide film being bonded to the first substrate by an action of a functional group.

In one embodiment, a lower surface of the first substrate is an amino modified surface.

In one embodiment, the influenza virus detection chip further includes a second substrate disposed opposite to the first substrate, wherein the graphene oxide film, the first pad, the first electrode and the second electrode are interposed between the first substrate and the second substrate.

In one embodiment, the influenza virus detection chip further includes a second pad configured to absorb a sample solution, wherein the second pad, the first pad and the graphene oxide film are disposed sequentially in the first direction.

In one embodiment, the influenza virus detection chip further includes an third pad configured to absorb an excess sample solution, wherein the first pad, the graphene oxide film and the third pad are disposed sequentially in the first direction.

In one embodiment, the first electrode and the second electrode are respectively adjacent to and in contact with the both ends of the graphene oxide film in the second direction perpendicular to the first direction.

In one embodiment, the first substrate and the second substrate include at least one of a glass substrate, a silicon substrate or an organic polymer substrate.

In one embodiment, one of the first substrate and the second substrate is transparent.

In one embodiment, the influenza virus detection chip further includes a second pad configured to absorb a sample solution and an third pad configured to absorb an excess sample solution, wherein the second pad, the first pad, the graphene oxide film and the third pad are disposed sequentially in the first direction.

In one embodiment, both the second pad and the first pad are independent or integrated layers made of polyester fiber.

In one embodiment, the second pad, the first pad and the third pad have a same thickness.

In one embodiment, the second pad and the second pad and the first pad are combined in a manner of overlapping each other.

In one embodiment, the first pad and the graphene oxide film are combined in a manner of overlapping each other.

In one embodiment, the graphene oxide film and the third pad are combined in a manner of overlapping each other.

In one embodiment, the first monoclonal antibody with a fluorescent label and the second monoclonal antibody are capable of specifically reacting to a same antigen.

According to another aspect, the present disclosure provides a method for detecting influenza virus using the above influenza virus detection chip, the method including:

flowing a sample solution sequentially through the first pad and the graphene oxide film;

irradiating the graphene oxide film with a laser while detecting a current across the graphene oxide film by using the first electrode and the second electrode; and determining that the sample solution contains influenza virus in the case where a change occurs in the current across the graphene oxide film.

In one embodiment, the influenza virus detection chip further includes a second pad configured to absorb a sample solution and an third pad configured to absorb an excess sample solution, wherein the second pad, the first pad, the graphene oxide film and the third pad are disposed sequentially in the first direction.

In one embodiment, both the second pad and the first pad are independent or integrated layers made of polyester fiber.

In one embodiment, the first pad, the second pad, the graphene oxide film and the third pad are configured in at least one of the following manners: the second pad and the first pad are combined in a manner of overlapping each other, the first pad and the graphene oxide film are combined in a manner of overlapping each other, or the graphene oxide film and the third pad are combined in a manner of overlapping each other.

It is to be understood that both the foregoing general description and the following detailed description are exemplary and explanatory only and are not restrictive of the disclosure, as claimed.

This section provides a summary of various implementations or examples of the technology described in the disclosure, and is not a comprehensive disclosure of the full scope or all features of the disclosed technology.

DETAILED DESCRIPTION

Figure 1:
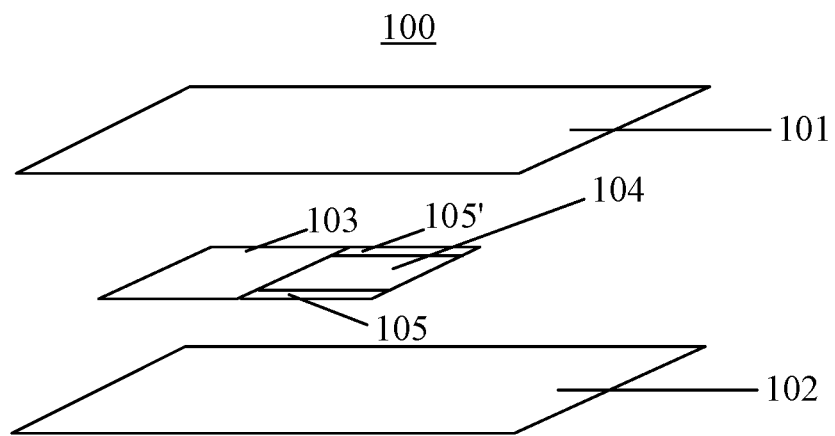
FIG. 1 is a schematic exploded perspective view showing an influenza virus detecting chip according to an embodiment of the present disclosure.

It will be understood that when an element or layer is referred to as being "on" or "connected" to another element or layer, the element or layer can be directly on the other element or layer, or directly connected to or coupled to the other element or layer, or an intermediate element or intermediate layer may also be present. In contrast, when an element is referred to as being "directly on" or "directly connected" or "directly coupled" to another element or layer, there is no intermediate element or intermediate layer. The same reference numerals are used to refer to the same elements. The term "and/or" as used herein includes any and all combinations of one or more of the associated listed items.

In the present disclosure, for convenience of description, spatially relative terms such as "lower", "above", "upper", "below", etc., may be used to describe the relationship between one element or feature and another elements or features as illustrated in the figures. It will be understood that the spatially relative terms are intended to encompass different orientations of the device in use or operation in addition to the orientation illustrated in the figures.

As used herein, the singular form of "a/an" and "the/said" is intended to include the plural form as well unless the context clearly indicates otherwise. It will also be understood that the terms such as "including" and/or "comprising", as used in the present disclosure, indicate the presence of the features, integers, steps, operations, elements and/or components, while does not exclude the presence or addition of one or more other features, integers, steps, operations, elements, components and/or combination thereof.

Hereinafter, the present disclosure will be described in detail with reference to the drawings.

FIG. 1 is a schematic exploded perspective view showing an influenza virus detecting chip according to an embodiment of the present disclosure Referring to FIG. 1, the influenza virus detecting chip 100 according to the present embodiment includes an upper substrate 101, a lower substrate 102, and a bonding pad 103 and a graphene oxide film 104 disposed sequentially in the first direction (e.g., the direction from left to right) in the same layer between the upper substrate 101 and the lower substrate 102. In addition, the influenza virus detecting chip 100 further includes a first electrode 105 and a second electrode 105' respectively connected to both ends of the graphene oxide film 104 in a second direction perpendicular to the first direction. In the embodiment, a monoclonal antibody with a fluorescent label is included in the bonding pad 103, and a monoclonal antibody is included on the graphene oxide film 104, wherein the fluorescent label has a C=C—C=C conjugated double bond.

Exemplarily, both the upper substrate 101 and the lower substrate 102 may be a glass substrate, a silicon substrate, or an organic polymer substrate. Specifically, the upper substrate 101 and the lower substrate 102 may each be selected from a silicon substrate, a glass substrate, a PET substrate, a PMMA substrate, or the like.

The bonding pad 103 is a film layer made of, for example, polyester fiber, but in the present disclosure, the material for forming the bonding pad 103 is not limited thereto.

A monoclonal antibody with a fluorescent label is included in the bonding pad 103, wherein the fluorescent label has a C=C—C=C conjugated double bond.

The first electrode 105 and the second electrode 105' may be formed of a general electrode material (for example, a metal, an alloy, a conductive metal oxide, a conductive metal nitride, or the like). For example, the first electrode 105 and the second electrode 105' may be formed of a metal such as titanium, platinum, rhodium, gold, silver, molybdenum, aluminum, tungsten, copper, ruthenium, chromium, rhenium, or an alloy including the above method, or may be formed of a conductive oxide such as indium zinc oxide, aluminum zinc oxide, indium tin oxide, gallium zinc oxide or zinc tin oxide.

Exemplarily, the first electrode 105 and the second electrode 105' may be formed by depositing an electrode material on the lower substrate 102 and then performing a photolithography process. Then, the graphene oxide film 104 may be formed on the lower substrate 102 by dropping a graphene oxide solution between the first electrode 105 and the second electrode 105' formed on the lower substrate 102 and drying the graphene oxide solution.

In the present embodiment, before the graphene oxide film 104 is formed on the lower substrate 102, the surface of the lower substrate 102 may be subjected to, for example, amino modification, so that the modified amino group on the surface of the lower substrate 102 can react with the groups such as the carboxyl group or the epoxy group on the surface of the graphene oxide film 104. Accordingly, graphene oxide film 104 is bonded to the lower substrate 102 by the action of these functional groups.

The monoclonal antibody can also be bound to the graphene oxide film 104 by the action of a functional group.

In addition, in order to allow the sample solution to flow smoothly, the bonding pad 103 and the graphene oxide film 104 may be partially overlapped at positions in contact with each other, that is, the bonding pad 103 and the graphene oxide film 104 may be combined in such a manner as to overlap each other, which may facilitate the flow of the sample solution.

The upper substrate 101 and the lower substrate 102 may be bonded together by, for example, an adhesive, and the bonding pad 103 and the graphene oxide film 104 are sandwiched between the upper substrate 101 and the lower substrate 102.

In the present embodiment, the first electrode 105 and the second electrode 105' are respectively adjacent to and in contact with both ends of the graphene oxide film 104 in the second direction perpendicular to the first direction, and are interposed between the upper substrate 101 and the lower substrates 102. Of course, the first electrode 105 and the second electrode 105' may be disposed in other manners as long as the current across the graphene oxide film 104 (or the resistance of the graphene oxide film 104) can be detected.

When the influenza virus detection chip 100 of the present embodiment is used for influenza virus detection, a sample solution to be detected (e.g., saliva or blood, etc.) may be added to the influenza virus detection chip 100, so that the sample solution to be detected first flows to the bonding pad. When the sample solution to be detected contains the influenza virus (i.e., an antigen), the antigen specifically reacts with the fluorescently labeled monoclonal antibody in the bonding pad, and then the sample solution continues to flow to the graphene oxide film 104 by capillary action and reacts specifically with the monoclonal antibody thereon to generate a double-antibody sandwich influenza virus complex.

The generated double-antibody sandwich influenza virus complex is fixed on the surface of the graphene oxide film 104, and when a laser is irradiated to these complexes, both the fluorescent label flowing onto the graphene oxide film 104 and the graphene oxide film 104 have $C=C-C=C$ conjugated double bonds, and the distance therebetween is very close, resulting in stacking of $C=C-C=C$ conjugated double bonds, and then fluorescence energy resonance transfer, that is, fluorescence quenching occurs. In order to facilitate laser irradiation to the composite, one of the upper substrate 101 and the lower substrate 102 may be transparent. Of course, the upper substrate 101 and the lower substrate 102 may both be transparent.

When fluorescence energy resonance transfer occurs, the photon energy generated by the fluorescent label is absorbed by the graphene oxide, resulting in a decrease in the electrical resistance of the graphene oxide. When the electric resistance of the graphene oxide is decreased, a change of the current across the graphene oxide film 104 can be detected by using the first electrode 105 and the second electrode 105'. That is, when the current across the graphene oxide film 104 changes, it can be determined that the influenza virus is contained in the sample solution.

In one embodiment of the present disclosure, the fluorescently labeled monoclonal antibody in the bonding pad and the monoclonal antibody on the graphene oxide film may be antibodies capable of specifically reacting to the same antigen. The fluorescently labeled monoclonal antibody in the bonding pad and the monoclonal antibody on the graphene oxide film may be the same antibody, for example, the antibody against the NP protein of the avian influenza virus. The fluorescently labeled monoclonal antibody may be fluorescently labeled 1G11, and the monoclonal antibody on the graphene oxide film may also be 1G11, but not fluorescently labeled, i.e., the two antibodies are identical. However, the present disclosure is not limited thereto, and the two antibodies may also be different antibodies capable of specifically reacting to the same antigen.

Figure 2:
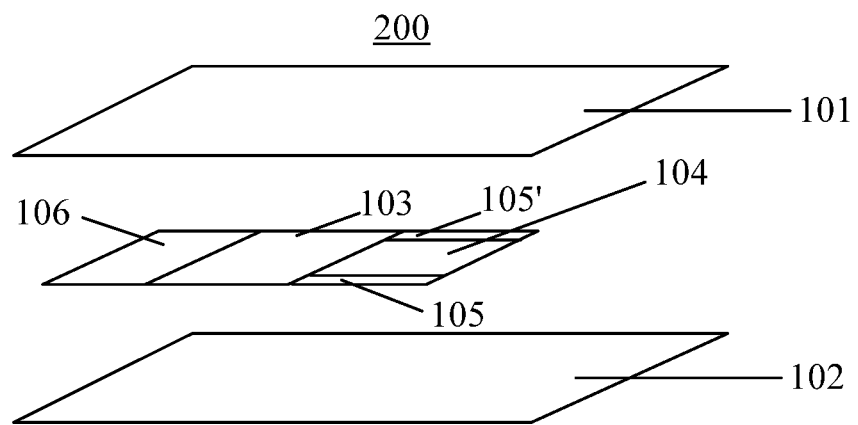
FIG. 2 is a schematic exploded perspective view showing an influenza virus detecting chip according to an embodiment of the present disclosure.

FIG. 2 is a schematic exploded perspective view showing an influenza virus detecting chip according to an embodiment of the present disclosure.

In the present embodiment, in addition to the above-described components in the foregoing embodiments, the influenza virus detecting chip 200 further includes a sample pad 106 for absorbing a sample solution. The sample pad 106 is disposed on the left side of the bonding pad 103 and is in contact with the bonding pad 103. That is, the sample pad 106, the bonding pad 103, and the graphene oxide film 104 are sequentially disposed in the first direction (i.e., from left to right).

In the present embodiment, the sample pad 106 may also be made of polyester fiber, but is not limited thereto. When the sample pad 106 and the bonding pad 103 are made of the same material, they may be formed separately or integrally. That is, the sample pad 106 and the bonding pad 103 may be formed as independent or integrated film layers.

When the sample pad 106 and the bonding pad 103 are formed as a single film layer, the fluorescently labeled monoclonal antibody can be bonded to a region of the single film layer close to the graphene oxide film 104 while not being bounded to a region of the single film layer away from the graphene oxide film 104. In this case, the single film layer has two regions, one of which contains the fluorescently labeled monoclonal antibody and the other of which does not contain the fluorescently labeled monoclonal antibody.

In the present embodiment, the sample pad 106 and the bonding pad 103 may have the same thickness so as to be well sealed by the upper substrate 101 and the lower substrate 102.

Further, in the present embodiment, when the sample pad 106 and the bonding pad 103 are two mutually independent components, the sample pad 106 and the bonding pad 103 may be combined in such a manner as to overlap each other to facilitate the smooth flow of the sample solution to be detected. Of course, in the present embodiment, the bonding pad 103 and the graphene oxide film 104 may also be combined in such a manner as to overlap each other.

When the influenza virus detection chip 200 of the present embodiment is used for influenza virus detection, the sample solution to be detected will first flow to the sample pad 106, and then flow to the bonding pad 103 by capillary action, and the subsequent process is substantially the same as the process described in the foregoing embodiment, which will not be described again.

Figure 3:
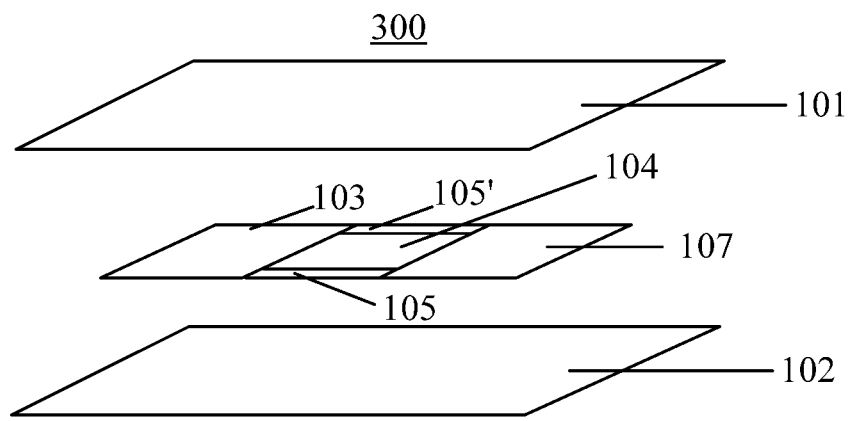
FIG. 3 is a schematic exploded perspective view showing an influenza virus detecting chip according to an embodiment of the present disclosure.

FIG. 3 is a schematic exploded perspective view showing an influenza virus detecting chip according to an embodiment of the present disclosure.

In the present embodiment, in addition to the above-described components in the foregoing embodiments, the influenza virus detecting chip 300 further includes an absorbent pad 107 for absorbing an excess sample solution. The absorbent pad 107 is disposed on the right side of the graphene oxide film 104 and is in contact with the graphene oxide film 104. That is, the bonding pad 103, the graphene oxide film 104, and the absorbent pad 107 are sequentially disposed in the first direction (i.e., from left to right).

In the present embodiment, the absorbent pad 107 may be made of a composite fiber material, but is not limited thereto, and may be made of any material capable of absorbing fluid.

In the present embodiment, the absorbent pad 107 and the bonding pad 103 may have the same thickness so as to be well sealed by the upper substrate 101 and the lower substrate 102.

When the influenza virus detecting chip 300 of the present embodiment is used for influenza virus detection, the excess sample solution can be absorbed by the absorbent pad 107. Further, the absorbent pad 107 and the graphene oxide film 104 may be combined in such a manner as to overlap each other to facilitate the smooth absorption of the excess sample solution by the absorbent pad 107.

Figure 4:
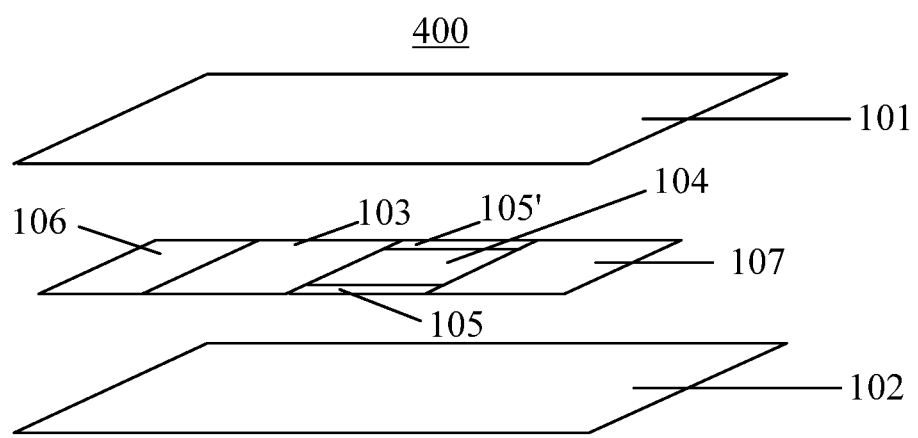
FIG. 4 is a schematic exploded perspective view showing an influenza virus detecting chip according to an embodiment of the present disclosure.

FIG. 4 is a schematic exploded perspective view showing an influenza virus detecting chip according to an embodiment of the present disclosure.

In the present embodiment, in addition to the above-described components in the foregoing embodiments, the influenza virus detecting chip 400 further includes an absorbent pad 107 for absorbing an excess sample solution. The absorbent pad 107 is disposed on the right side of the graphene oxide film 104 and is in contact with the graphene oxide film 104. That is, the sample pad 106, the bonding pad 103, the graphene oxide film 104, and the absorbent pad 107 are sequentially disposed in the first direction (i.e., from left to right).

The absorbent pad 107 can be formed and arranged in the same manner as described in the foregoing embodiments.

In the present embodiment, the sample pad 106, the bonding pad 103, and the absorbent pad 107 have the same thickness so as to be well sealed by the upper substrate 101 and the lower substrate 102. Further, in order to facilitate the smooth flow of the sample solution, the sample pad 106 and the bonding pad 103 may be combined in such a manner as to overlap each other, and the bonding pad 103 and the graphene oxide film 104 may be combined in such a manner as to overlap each other, and/or the graphene oxide film 104 and the absorbent pad 107 may be combined in such a manner as to overlap each other.

When the influenza virus detection chip 400 of the present embodiment is used for influenza virus detection, the sample solution to be detected will first flow to the sample pad 106, and then flow to the bonding pad 103 by capillary action, and the subsequent process is the same as the process described in the foregoing embodiment. In addition, excess sample solution can be absorbed by the absorbent pad 107.

The influenza virus detecting chip of the present disclosure and a method for detecting an influenza virus therewith have high detection sensitivity, and the detection is simple, quick, and convenient. In addition, the presence or absence of the influenza virus can be detected by detecting the change of the current when a small amount of virus is contained in the sample. The detection sensitivity is increased, and early detection and prevention can be performed to prevent the continuous infection of the influenza virus.

The foregoing description of the specific exemplary embodiments of the present disclosure has been presented with reference to the drawings. These exemplary embodiments are not intended to be exhaustive or to limit the scope of the present disclosure to the particularly disclosed form. In addition, it is apparent that many amendments and changes are available to those of ordinary skill in the art under the above teaching. Therefore, the scope of the present disclosure is not intended to be limited to the foregoing embodiments, but is intended to be defined by the claims and their equivalents.

What is claimed is:

1. An influenza virus detection chip comprising:
   a graphene oxide film;
   a first pad disposed on one side of the graphene oxide film in a first direction; and
   a first electrode and a second electrode, connected to both ends of the graphene oxide film in a second direction perpendicular to the first direction,
   wherein a first monoclonal antibody with a fluorescent label is included in the first pad, and a second monoclonal antibody is included in the graphene oxide film, and wherein the fluorescent label comprises a C=C—C=C conjugated double bond, and wherein the first monoclonal antibody and the second monoclonal antibody are capable of specifically binding to influenza virus.

2. The influenza virus detection chip according to claim 1, further comprising a first substrate, the graphene oxide film being bonded to the first substrate by an action of a functional group.

3. The influenza virus detection chip according to claim 2, further comprising a second substrate disposed opposite to the first substrate, wherein the graphene oxide film, the first pad, the first electrode and the second electrode are interposed between the first substrate and the second substrate.

4. The influenza virus detection chip according to claim 1, further comprising a second pad configured to absorb a sample solution, wherein the second pad, the first pad and the graphene oxide film are disposed sequentially in the first direction.

5. The influenza virus detection chip according to claim 1, further comprising an third pad configured to absorb an excess sample solution, wherein the first pad, the graphene oxide film and the third pad are disposed sequentially in the first direction.

6. The influenza virus detection chip according to claim 1, wherein the first electrode and the second electrode are respectively adjacent to and in contact with the both ends of the graphene oxide film in the second direction perpendicular to the first direction.

7. The influenza virus detection chip according to claim 3, wherein the first substrate and the second substrate comprise at least one of a glass substrate, a silicon substrate or an organic polymer substrate.

8. The influenza virus detection chip according to claim 7, wherein one of the first substrate and the second substrate is transparent.

9. The influenza virus detection chip according to claim 1, further comprising a second pad configured to absorb a sample solution and an third pad configured to absorb an excess sample solution, wherein the second pad, the first pad, the graphene oxide film and the third pad are disposed sequentially in the first direction.

10. The influenza virus detection chip according to claim 9, wherein both the second pad and the first pad are independent or integrated layers made of polyester fiber.

11. The influenza virus detection chip according to claim 9, wherein the second pad, the first pad and the third pad have a same thickness.

12. The influenza virus detection chip according to claim 9, wherein the second pad and the first pad are combined in a manner of overlapping each other.

13. A method for detecting influenza virus using the influenza virus detection chip according to claim 1, comprising:
   flowing a sample solution sequentially through the first pad and the graphene oxide film;
   irradiating the graphene oxide film with a laser while detecting a current across the graphene oxide film by using the first electrode and the second electrode; and
   determining that the sample solution contains influenza virus in the case where a change occurs in the current across the graphene oxide film.

14. The method according to claim 13, wherein the influenza virus detection chip further comprises a second pad configured to absorb a sample solution and an third pad configured to absorb an excess sample solution, wherein the second pad, the first pad, the graphene oxide film and the third pad are disposed sequentially in the first direction.

15. The method according to claim 14, wherein both the second pad and the first pad are independent or integrated layers made of polyester fiber.

16. The method according to claim 14, wherein the first pad, the second pad, the graphene oxide film and the third pad are configured in at least one of the following manners: the second pad and the first pad are combined in a manner of overlapping each other, the first pad and the graphene oxide film are combined in a manner of overlapping each other, or the graphene oxide film and the third pad are combined in a manner of overlapping each other.

17. The influenza virus detection chip according to claim 2, wherein a lower surface of the first substrate is an amino modified surface.

18. The influenza virus detection chip according to claim 9, wherein the first pad and the graphene oxide film are combined in a manner of overlapping each other.

19. The influenza virus detection chip according to claim 9, wherein the graphene oxide film and the third pad are combined in a manner of overlapping each other.

20. The influenza virus detection chip according to claim 1, wherein the first monoclonal antibody with a fluorescent label and the second monoclonal antibody are capable of specifically binding to the same antigen.

* * * * *